(12) United States Patent
Kim

(10) Patent No.: US 9,164,091 B2
(45) Date of Patent: *Oct. 20, 2015

(54) CENTRIFUGAL MICRO-FLUIDIC DEVICE AND METHOD FOR DETECTING ANALYTES FROM LIQUID SPECIMEN

(75) Inventor: In Wook Kim, Seongnam-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 510 days.

This patent is subject to a terminal disclaimer.

(21) Appl. No.: 13/004,933

(22) Filed: Jan. 12, 2011

(65) Prior Publication Data
US 2011/0189701 A1    Aug. 4, 2011

(30) Foreign Application Priority Data

Jan. 29, 2010  (KR) .......................... 10-2010-008392

(51) Int. Cl.
| | |
|---|---|
| *G01N 33/543* | (2006.01) |
| *G01N 33/558* | (2006.01) |
| *B01L 3/00* | (2006.01) |
| *G01N 35/00* | (2006.01) |

(52) U.S. Cl.
CPC ...... *G01N 33/54366* (2013.01); *B01L 3/50273* (2013.01); *G01N 33/558* (2013.01); *G01N 35/00069* (2013.01); *B01L 3/502738* (2013.01); *B01L 2200/10* (2013.01); *B01L 2300/0806* (2013.01); *B01L 2300/0867* (2013.01); *B01L 2400/0406* (2013.01); *B01L 2400/0409* (2013.01); *B01L 2400/086* (2013.01); *B01L 2400/088* (2013.01); *G01N 2035/00495* (2013.01); *Y10T 436/111666* (2015.01); *Y10T 436/25375* (2015.01)

(58) Field of Classification Search
CPC .................. G01N 33/54366; G01N 35/00069; G01N 33/558; B01L 3/50273
See application file for complete search history.

(56) References Cited

U.S. PATENT DOCUMENTS

| | | |
|---|---|---|
| 5,985,675 A | 11/1999 | Charm et al. |
| 7,077,996 B2 | 7/2006 | Randall et al. |
| 2002/0106786 A1 | 8/2002 | Carvalho et al. |
| 2003/0152491 A1 | 8/2003 | Kellogg et al. |
| 2003/0180814 A1* | 9/2003 | Hodges et al. .................. 435/7.9 |
| 2004/0089616 A1 | 5/2004 | Kellogg et al. |

(Continued)

FOREIGN PATENT DOCUMENTS

| | | |
|---|---|---|
| CN | 101522916 A | 9/2009 |
| EP | 1284818 B1 | 2/2003 |

(Continued)

OTHER PUBLICATIONS

International Search Report (PCT/ISA/210) issued on Sep. 27, 2011 in the International Patent Application No. PCT/KR2011/000192.

(Continued)

*Primary Examiner* — Melanie Y Brown
(74) *Attorney, Agent, or Firm* — Sughrue Mion, PLLC

(57) ABSTRACT

A centrifugal micro-fluidic device detecting analytes in a liquid specimen and a method of detection of analytes from a liquid specimen using the micro-fluidic device are provided. Reaction efficiency is increased using a repetitive flow of the liquid specimen induced by an alternating combination of capillary force and centrifugal force, thereby enhancing detection sensitivity.

31 Claims, 8 Drawing Sheets

(56) References Cited

U.S. PATENT DOCUMENTS

| | | | |
|---|---|---|---|
| 2005/0163658 A1* | 7/2005 | Wang et al. | 422/56 |
| 2008/0056949 A1 | 3/2008 | Lee et al. | |
| 2008/0108120 A1 | 5/2008 | Cho et al. | |
| 2008/0233594 A1* | 9/2008 | Inganas | 435/7.1 |
| 2008/0300148 A1 | 12/2008 | Lee et al. | |
| 2009/0181411 A1* | 7/2009 | Battrell et al. | 435/7.92 |
| 2009/0191643 A1 | 7/2009 | Boehm et al. | |
| 2009/0221431 A1* | 9/2009 | Yoo | 506/9 |
| 2009/0317896 A1* | 12/2009 | Yoo | 435/287.1 |
| 2011/0263030 A1* | 10/2011 | Kim | 436/45 |

FOREIGN PATENT DOCUMENTS

| | | | |
|---|---|---|---|
| JP | 2009014690 A | 1/2009 | |
| JP | 2009-128367 A | 6/2009 | |
| JP | 2009545742 A | 12/2009 | |
| WO | 2006/121266 A1 | 11/2006 | |
| WO | 2008/016271 A1 | 2/2008 | |

OTHER PUBLICATIONS

Communication, dated Mar. 1, 2013, issued by the Canadian Intellectual Property Office in counterpart Canadian Patent Application No. 2,788,344.
Communication, dated Jun. 21, 2013, issued by the Australian Patent Office in counterpart Australian Patent Application No. 2011211319.
Communication, dated May 22, 2013, issued by the European Patent Office in counterpart European Patent Application No. 13160827.5.
Communication, dated May 21, 2013, issued by the European Patent Office in counterpart European Patent Application No. 11737241.7.
Communication dated Nov. 26, 2013 issued by the State Intellectual Property Office of P.R China in counterpart Chinese Application No. 201180002706.6.
Communication dated Jan. 7, 2014 issued by the Canadian Intellectual Property Office in counterpart Canadian Application No. 2,788,344.
Communication, Issued by the Japanese Patent Office, Dated Sep. 2, 2014, in counterpart Japanese Application No. 2012-551077.
Communication from the Japanese Patent Office dated May 25, 2015 in a counterpart Japanese application No. 2012-551077.
Stefan Haeberle, et al., "Microfluidic platforms for lab-on-a-chip applications", Lab on a Chip, vol. 7, Jun. 25, 2007, pp. 1094-1110, XP007902894.
Communication from the European Patent Office issued Jun. 10, 2015 in a counterpart European Application No. 13 160 827.5.

* cited by examiner

CENTRIFUGAL MICRO-FLUIDIC DEVICE AND METHOD FOR DETECTING ANALYTES FROM LIQUID SPECIMEN

CROSS-REFERENCE TO RELATED APPLICATION

This application claims priority from Korean Patent Application No. 10-2010-008392 filed on Jan. 29, 2010 in the Korean Intellectual Property Office, the disclosure of which is incorporated herein by reference.

BACKGROUND

1. Field

Apparatuses and methods consistent with exemplary embodiments relate generally to a centrifugal micro-fluidic device for detecting analytes in a liquid specimen and a detection method using the micro-fluidic device and, more particularly, to a centrifugal micro-fluidic device for detection of analytes from a liquid specimen with improved sensitivity. wherein a repeated flow of a liquid specimen induced by both capillary force and centrifugal force enhances reaction efficiency, as well as a method for detection of analytes in a liquid specimen using the micro-fluidic device.

2. Description of the Related Art

In order to cause a fluid to flow or move in a micro-fluidic structure of a micro-fluidic device, a driving pressure is generally required. The driving pressure may be a capillary pressure or pressure generated using an additional pump. In recent years, clinical diagnostic analyzers have been proposed that are designed to enable detection of a target material present in a small amount of fluid in simple and economical ways. One example is a centrifugal micro-fluidic device having a micro-fluidic structure mounted on a circular disc-type rotational platform such as a lab-on-disc and/or a lab compact disc ("CD").

Lab-on-disc, meaning "laboratory on a disk" is a CD-type device in which various experimental units are integrated for analysis of biomolecules used in a laboratory in order to execute several experimental processes including, for example, isolation, purification, mixing, labeling, assaying and/or washing of a sample on a small disc. Upon introduction of a biological sample, such as blood, into a micro-fluidic structure placed on a disc, the CD-type device may advantageously transfer a fluid such as a biological sample, a chemical reagent, etc. Centrifugal force alone may be used to induce driving pressure and transport the fluid without additional driving systems.

Recently, the use of a 'lap-on-a-chip' for blood analysis has been investigated for its ability to rapidly obtain a variety of information from blood samples collected from clinical cases. As a result, a rapid-chip or a rapid-kit has been developed. For such a rapid-chip or rapid-kit, several processes are executed in only a reaction part of the rapid-chip or rapid-kit, including: combination of a material to be analyzed (that is, an analyte) with a detectable signal generator; combination of a composite of the analyte and the detectable signal generator (referred to as "detectable signal generator-analyte complex") with a capture binder and washing thereof; and the like. However, since the analyte is primarily combined with the labeling reagent, a large amount of labeling reagent is required, although this requirement is seldom satisfied in view of practical aspects. In addition, if the analyte does not fully react with the labeling reagent, an un-combined portion of the analyte and the detectable signal generator may be combined with a capture binder present on a test line, in turn competitively inhibiting the detectable signal generator-analyte complex from being bonded to a control line or test line. Furthermore, combination of the analyte and each reagent is terminated within only a single fluid sample stream in one direction, thus resulting in insufficient combination and causing decrease in sensitivity and difficulties in quantitative analysis. The kit does not have an active device for controlling a re-lysis rate of the detectable signal generator and, therefore, the detectable signal generator is excessively re-lysed by a constant volume of a fluid sample flowing thereto, thus causing waste of the detectable signal generator at an early stage. On the other hand, re-lysis of the detectable signal generator is drastically reduced in a later stage, thus entailing difficulties in sensitive detection of the analyte.

SUMMARY

One or more exemplary embodiments provide a centrifugal micro-fluidic device for detection of analytes from a liquid specimen with improved sensitivity wherein a repeated flow of the liquid specimen induced by a combination of capillary force and centrifugal force enhances reaction efficiency, as well as a method for detection of analytes from a liquid specimen using the micro-fluidic device.

According to an aspect of an exemplary embodiment, there is provided a centrifugal micro-fluidic device including: a rotational body; at least one micro-fluidic structure including multiple chambers, at least one channel through which the multiple chambers are connected with one another and at least one valve opening and closing the at least one channel; wherein the plurality of chambers include a reaction chamber where a detectable signal generator is combined with an analyte of a liquid specimen to create a detectable signal generator-analyte complex, and an analysis chamber located downstream from the reaction chamber; wherein the analysis chamber includes a detection region where a capture binder is combined with the detectable signal generator-analyte complex; wherein the detection region includes one of porous membranes, micro-pore structures and micro-pillars; and a detection unit.

According to an aspect of another exemplary embodiment, there is provided a centrifugal micro-fluidic device including: at least one micro-fluidic structure having multiple chambers, at least one channel through which the multiple chambers are connected and at least one valve for opening and closing the at least one channel; wherein the plurality of chambers comprise a reaction chamber where a detectable signal generator is combined with an analyte of a liquid specimen to create a detectable signal generator-analyte complex, and an analysis chamber located downstream from the reaction chamber; wherein the analysis chamber includes a detection region where a capture binder is combined with the detectable signal generator-analyte complex; wherein the at least one valve controls the transportation of the fluid between the reaction chamber and the analysis chamber; wherein the detection region includes one of porous membranes, micro-pore structures and micro-pillars; and a detection unit detects absorbance the detection region of the reaction chamber.

According to an aspect of another exemplary embodiment, there is provided a centrifugal micro-fluidic device including: a rotational body; at least one micro-fluidic structure having multiple chambers, and at least one channel through which the multiple chambers are connected together; wherein the plurality of chambers include a reaction chamber where a detectable signal generator is combined with an analyte of a liquid specimen to create a detectable signal generator-analyte complex, and an analysis chamber located downstream from the reaction chamber; wherein the analysis chamber includes a detection region where a capture binder is combined with the detectable signal generator-analyte complex; wherein the detection region includes one of porous membranes, micro-pore structures and micro-pillars; and a detection unit which detects absorbance the detection region of the reaction chamber.

The capture binder and the detectable signal generator may be selected from deoxyribonucleic acid (DNA), oligonucleotide, ribonucleic acid (RNA), RNA aptamer, peptide nucleic acid (PNA), ligand, receptor, hapten, antigen and antibody; however, they are not particularly limited thereto.

The analysis chamber may further include holder which carries a fluid provided from the reaction chamber.

The detection region may contact the holder at one end of the holder.

The detection region may further include a test region to which the capture binder is fixed, as well as a control region located downstream of the test region relative to a direction for capillary action apart from the test region by a distance.

A section of the detection region including the test region and the control region may be inclined in the direction of capillary action.

The plurality of chambers may further include a stoppage chamber which is located downstream of the analysis chamber relative to a direction of centrifugal force to receive the liquid specimen from the analysis chamber.

The detectable signal generator in the reaction chamber is contained in a liquid or dried solid state.

The detectable signal generator may include polymeric beads, metal colloids, enzymes, fluorescent materials, luminous materials, super paramagnetic materials, materials containing lanthanum (III) chelate, polymeric nano-particles, or radioactive isotopes.

The detection unit may detect and assay a detectable signal generator-analyte complex combined with the capture binder.

The detection unit may include a light source unit and a light receiving unit, such that the light receiving unit is aligned with the light source unit to accept light emitted from the light source unit that passes through the analysis chamber.

According to an aspect of another exemplary embodiment, there is provided a method of analyzing an analyte in a liquid specimen, including: injecting the liquid specimen into a micro-fluidic structure of the micro-fluidic device, centrifuging the liquid specimen to obtain a supernatant; transporting the supernatant into a reaction chamber in which a detectable signal generator is contained; combining the analyte in the supernatant with the detectable signal generator to create a detectable signal generator-analyte complex; subjecting the micro-fluidic device to centrifugation; transporting the detectable signal generator-analyte complex into an analysis chamber, wherein the analysis chamber is located downstream of the reaction chamber, and wherein the analysis chamber includes a detection region to which a capture binder is fixed, and wherein the detection region includes porous membranes, micro-pore structures or micro-pillars; moving the and wherein the analysis chamber by capillary force to an end of the analysis chamber; combining the detectable signal generator-analyte complex in the supernatant with the capture binder in the analysis chamber; applying centrifugal force to the micro-fluidic device to deliver the supernatant moved to the end of the analysis chamber to a front end of the analysis chamber and simultaneously combining the detectable signal generator-analyte complex in the supernatant with the capture binder in the analysis chamber; and detecting the detectable signal generator-analyte complex combined with the capture binder.

The movement of the supernatant from an end of the analysis chamber to the other end of the analysis chamber may proceed at least two times.

The analysis chamber may further include a holder which carries a fluid provided from the reaction chamber.

The detection region may contact the holder at one end of the holder.

For the centrifugal micro-fluidic device, the micro-fluidic structure may further include a stoppage chamber which is located downstream of the analysis chamber relative to a direction of centrifugal force to receive the liquid specimen from the analysis chamber.

The detectable signal generator in the reaction chamber is contained in a liquid or dried solid state.

The detectable signal generator may include polymeric beads, metal colloids, enzymes, fluorescent materials, luminous materials, super paramagnetic materials, materials containing lanthanum (III) chelate, polymeric nano-particles, or radioactive isotope elements.

Before detecting the detectable signal generator-analyte complex, the liquid specimen contained in the analysis chamber may be transported into the stoppage chamber so as to stop a reaction between the detectable signal generator-analyte complex and the capture binder.

BRIEF DESCRIPTION OF THE DRAWINGS

The above and/or other aspects will become apparent and more readily appreciated from the following description of the exemplary embodiments, taken in conjunction with the accompanying drawings, of which.

DETAILED DESCRIPTION

Hereinafter, and practical methods thereof will be exemplary embodiments will be described with reference to the accompanying drawings. However, the inventive concept may be embodied in various other forms, which are not particularly restricted to those described herein.

One exemplary embodiment provides a centrifugal micro-fluidic device for detection of an analyte from a liquid specimen, which includes a rotational body; at least one micro-fluidic structure having multiple chambers, at least one channel through which the multiple chambers are connected together and at least one valve for opening and closing the channel; and a detection unit, wherein the device also has a reaction chamber for receiving a detectable signal generator to be combined with the analyte in the liquid specimen and an analysis chamber that is located downstream of the reaction chamber and includes a detection region to which a capture binder to be combined with a detectable signal generator-analyte complex is fixed, and wherein a fluid transported between the reaction chamber and the analysis chamber is controlled by the above valve and the detection region includes porous membranes, micro-pore structures or micro-pillars.

A test sample may include, for example, DNA, oligonucleotide, RNA, PNA, ligand, receptor, antigen, antibody, milk, urine, saliva, hair, a crop sample, a meat sample, an avian sample, a livestock sample, a processed food sample, an oral cell, a tissue sample, sperm, protein or other bio materials; however, the test sample is not particularly limited thereto. Such a sample may be used in a liquid or fluid state by dissolution using a buffer solution. The analyte may include, for example, protein, antigen, antibody, DNA or RNA, oligonucleotide, receptor, and the like; although the analyte is not particularly limited thereto. For a urine sample, the analyte may be blood, glucose, ascorbic acid, ketone, protein, sugar, urobilinogen, bilirubin, etc.

Figure 1:
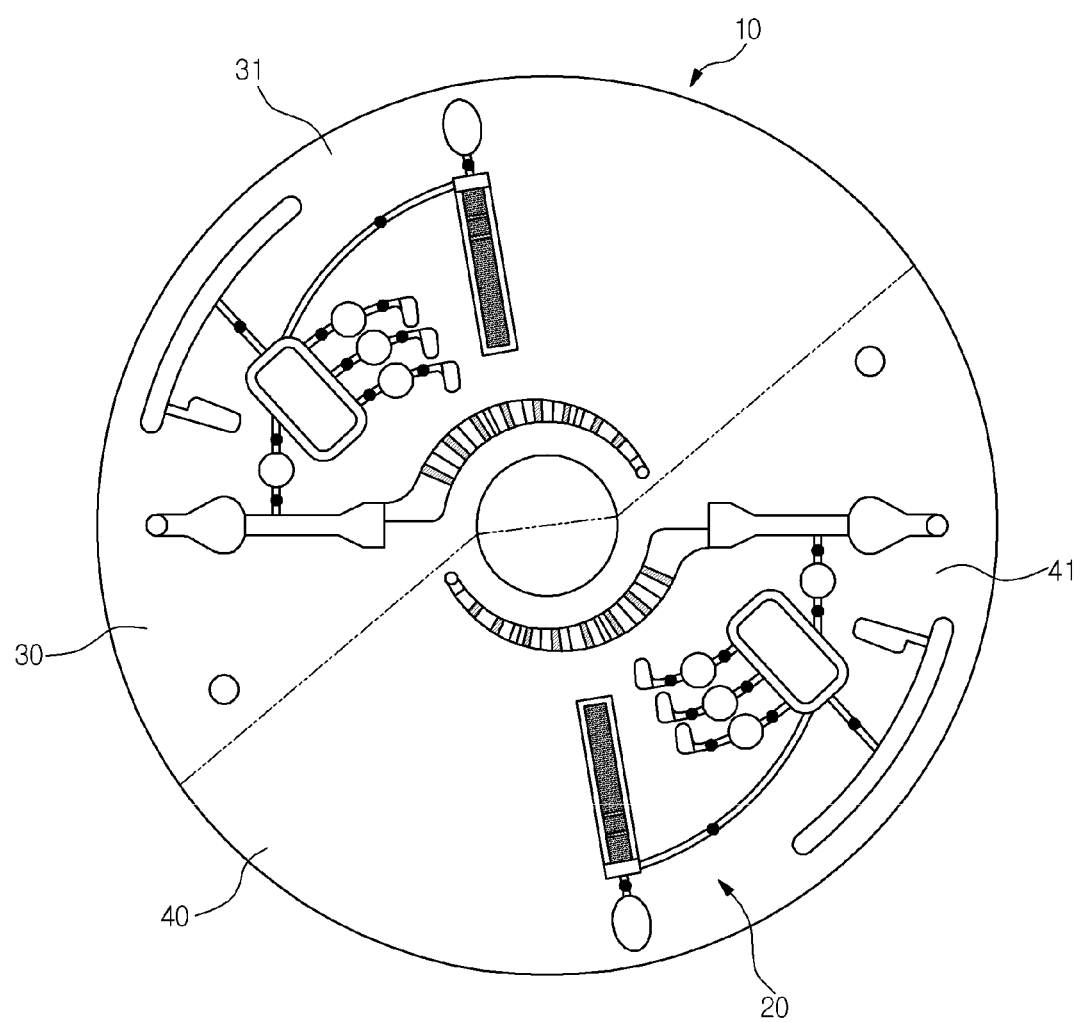
FIG. 1 is a schematic view illustrating the construction of a micro-fluidic device according to an exemplary embodiment.
Figure 2:
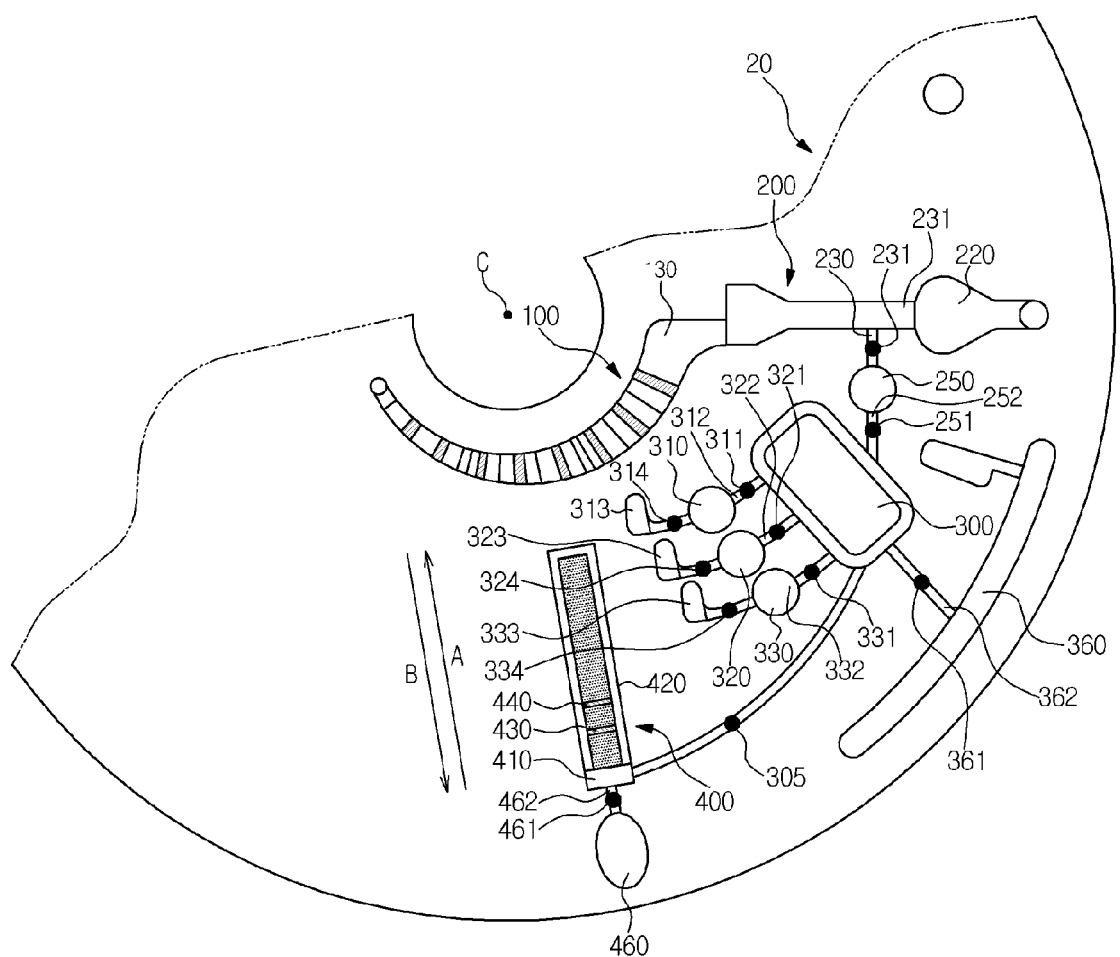
FIG. 2 is a schematic view illustrating the construction of a micro-fluidic structure in the micro-fluidic device shown in FIG. 1.

FIG. 1 is a schematic view illustrating the construction of a micro-fluidic device according to an exemplary embodiment, while FIG. 2 is a schematic view illustrating the construction of a micro-fluidic structure according to an exemplary embodiment.

A rotational body 10 used in one exemplary embodiment may include a circular disc-type platform 20 (see FIG. 1). However, a shape of the platform 20 is not particularly limited to a circular disc form. The platform may be formed using acryl or other plastic materials, each of which is easily formable and has a biologically inactive surface. However, a raw material for fabrication of the rotational body is not particularly limited and may include any materials with chemical or biological stability, optical transparency and/or mechanical workability.

At least one micro-fluidic structure 30 may be provided on the platform. For instance, after partitioning the platform 20 into several sections 30, 40, separate micro-fluidic structures 31, 41 may be placed independently of one another on the sections 30, 40, respectively. FIG. 1 shows a particular platform 20 having two micro-fluidic structures 31, 41 formed thereon.

The term "micro-fluidic structure" used herein refers to a general structure which consists of a plurality of chambers, channels and valves and induces a fluid flow, instead of a particular structural substance. Therefore, the "micro-fluidic structure" may form a specific unit with different functions or performances according to features such as the arrangement of chambers, channels and/or valves, and/or kinds of materials received in the structure.

Accordingly, the micro-fluidic device may be widely used in various applications, such as detection of various chemical compounds, environmentally harmful substances, blood analysis, urine testing, antigen-antibody response-based immunoassay, search of novel drug candidates based on ligand-receptor binding, DNA/RNA analysis, and so forth. Further, the micro-fluidic device may simultaneously detect and analyze at least two analytes.

The platform may be fabricated using at least one material selected from a variety of materials, such as plastic, polymethylmethacrylate ("PMMA"), glass, mica, silica, a silica wafer material, etc. The plastic material is used in view of economic merits and simple workability. Potential plastic materials may include polypropylene, polyacrylate, polyvinylalcohol, polyethylene, polymethylmethacrylate, polycarbonate, etc.

A fluid sample, a buffer solution, a reactive solution, etc. may be transported into separate chambers using centrifugal force generated by rotation of the rotational body 10. The rotational body 10 has a rotational driver D for high speed revolution (see FIG. 7). Centrifugal force generated by rotation of the rotational driver D may enable transportation and/or admixing of a sample.

FIG. 2 shows a sample chamber 100, a sample separation unit 200, a reaction chamber 300, and an analysis chamber 400.

The sample chamber 100 may provide a space to receive a fluid-type sample such as blood. The sample separation unit 200 may enable centrifugation of the sample into a supernatant (that is, serum, plasma, etc.) and a precipitate (that is, blood cells). The reaction chamber 300 and the analysis chamber 400 are structures for detecting specific protein, glucose, cholesterol, uric acid, creatinine, alcohol, etc. contained in the supernatant by antigen-antibody response, ligand-receptor binding, and so forth.

Figure 3:
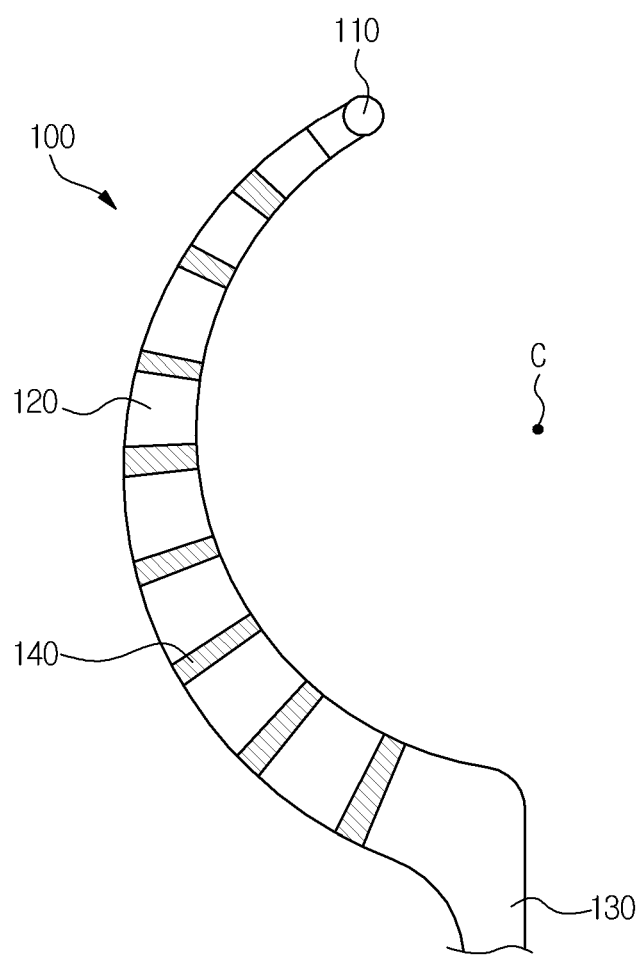
FIG. 3 is a detailed view illustrating a sample chamber.

FIG. 3 is a detailed view illustrating the sample chamber 100. Referring to FIG. 3, the sample chamber 100 has a sample introduction inlet 110 and a sample receiving unit 120. The sample receiving unit 120 has an outlet 130 connected to the sample separation unit 200 (not shown). Although not shown in the drawing, the outlet 130 may be formed to generate capillary force, so as to prevent a fluid sample from moving toward the sample separation unit 200 when centrifugal force is not applied, as described below. Alternatively, in order to control a flow of the fluid sample, a valve may be mounted on the outlet 130. Furthermore, the sample chamber 100 may have a cross-section increasing from the inlet 110 toward the outlet 130, enabling the sample contained in the sample receiving unit 120 to easily flow toward the sample separation unit 200 by centrifugal force. In order to facilitate the flow of the sample into the sample receiving unit 120 by injection pressure of the sample through the inlet 110 and, in addition, to block a reverse flow of the sample entered into the sample receiving unit 120 toward the inlet 110, an alternative structure to generate capillary pressure may be placed between the inlet 110 and the sample receiving unit 120. This alternative structure, such as a capillary valve-type structure, will pass the sample through the sample chamber 100 only when a desired pressure is applied.

The sample receiving unit 120 may have at least one anti-reverse flow unit 140 in a direction crossing a sample flow direction wherein the sample flows from the inlet 110 to the outlet 130. The anti-reverse flow unit 140 may be in a rib form. The anti-reverse flow unit 140 creates resistance in the flow of the sample, and as a result, inhibits a reverse flow of the sample from the sample receiving unit 120 to the inlet 110.

Figure 4:
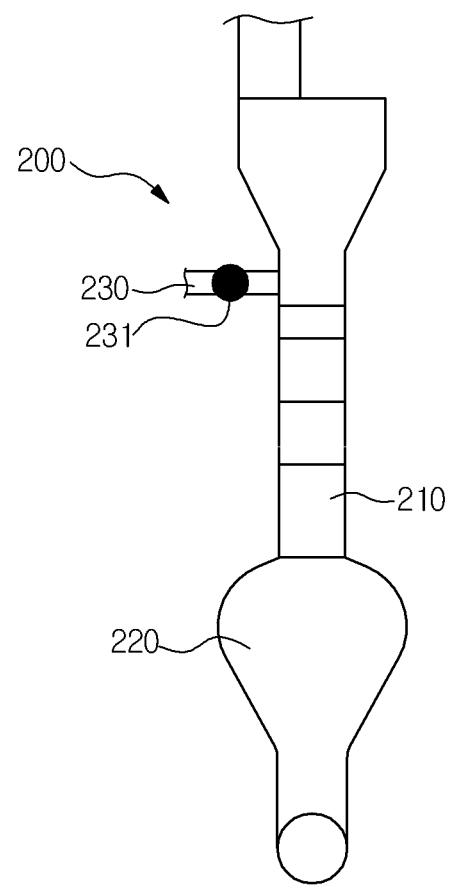
FIG. 4 is a detailed view illustrating a sample separation unit.

Since transportation of the sample from the sample chamber 100 to the sample separation unit 200 utilizes centrifugal force by rotation of the rotational body 10, the sample receiving unit 200 is duly located more outwardly than the sample chamber 100. The sample separation unit 200 for centrifugation of the sample may be configured in different forms, and an exemplary embodiment of the sample separation unit 200 is shown in FIG. 4. Referring to FIG. 4, the sample separation unit 200 may include a channel-type supernatant collector 210 outwardly extending from the sample chamber 100 and a precipitate collector 220, which is a space formed at an end of the supernatant collector 210 to collect a precipitate with relatively high specific gravity. The supernatant collector 210 has a sample dispenser channel 230 to distribute the supernatant into the reaction chamber 300 (not shown). The flow of the sample passing through the sample dispenser channel 230 may be controlled by a valve 231. The valve 231 may be any type of micro-fluidic valve. For instance, the valve 231 may comprise a so-called "normally closed valve" wherein a channel of the valve is closed to prevent a fluid from flowing unless the valve opens by an external power source.

Referring back to FIG. 2, a supernatant metering chamber 250 may be placed between the sample separation unit 200 and the reaction chamber 300, so as to measure an amount of the supernatant. A volume of the supernatant metering chamber 250 may be sufficient to carry a certain amount of the supernatant required for testing. A valve 251 is mounted on an outlet of the supernatant metering chamber 250, so as to control the fluid flow. The valve 251 may be a normally-closed valve identical to the valve 231. The supernatant metering chamber 250 is connected to the reaction chamber 300 through a channel 252. Although not shown in the drawing, an alternative chamber and an additional fluid channel may be provided between the sample dispenser channel 230 and the supernatant metering chamber 250, so as to receive excess sample in a liquid phase remaining after metering.

First and second buffer chambers 310 and 320 may receive a reactant (that is, a reactive solution) required for antigen-antibody response or a biochemical reaction (such as ligand-receptor binding).

The first buffer chamber 310 receives a first buffer. The first buffer may include, for example, a conjugate buffer for sandwich immunoassay, a competitive protein-containing buffer for competitive immunoassay, a buffer that contains various enzymes including, for example, polymerase and primer for DNA amplification, and so forth.

The first buffer chamber 310 is connected to a first vent chamber 313. The first vent chamber 313 forms a vent path to communicate the first buffer chamber 310 with external air, thus easily discharging the first buffer contained in the first buffer chamber 310. A valve 314 is placed between the first buffer chamber 310 and the first vent chamber 313. Another valve 311 is mounted on an outlet of the first buffer chamber 310. Each of such valves 311 and 314 may be normally closed valves as described above. By introducing the first buffer into the first buffer chamber 310 and installing the valves 311 and 314, the first buffer chamber 310 may remain sealed until the valves 311 and 314 are opened. According to another exemplary embodiment, a metering chamber (not shown) may be provided at the outlet of the first buffer chamber 310 in order to provide a constant amount of first buffer required for testing into the reaction chamber 300. If a valve (not shown) is mounted on an outlet of the metering chamber (not shown), the first buffer flow may be controlled. If the metering chamber is not used, the first buffer may be directly fed from the first buffer chamber 310 to the reaction chamber 300 by opening the valve 311 mounted on the outlet of the first buffer chamber 310.

The second buffer chamber 320 receives a second buffer. The second buffer may include, for example, a substrate buffer to express a specific color by reaction of the substrate with a product of conjugate reaction or competitive reaction, a buffer that contains various enzymes required for DNA hybridization, and so forth. The second buffer chamber 320 is substantially the same as the first buffer chamber 310 except that the second buffer received therein is different from the first buffer, and therefore a detailed description of the second buffer chamber 320 will be omitted for brevity.

Although one exemplary embodiment describes the microfluidic structure consisting of two buffer chambers 310 and 320, such structure may have only one buffer chamber or at least three buffer chambers, based on reaction types.

In another exemplary embodiment, a washer chamber 330 may contain a washing buffer to rinse a residue remaining after a reaction in the reaction chamber 300. The washer chamber 330 is connected with a third vent chamber 333. The third vent chamber 333 forms another vent path to communicate the washer chamber 330 with external air, thus easily discharging the washer buffer contained in the washer chamber 330. A valve 334 is placed between the washer chamber 330 and the third vent chamber 333. The washer chamber 330 is connected to the reaction chamber 300 through another valve 331. Each of such valves 331 and 334 may be a normally closed valve as described above.

The reaction chamber 300 receives the supernatant from the supernatant metering chamber 250 through a channel 252. The reaction chamber 300 may contain a detectable signal generator present in a liquid or solid phase.

When the detectable signal generator in a solid phase is present in the reaction chamber 300, the detectable signal generator may be temporarily fixed to an inner wall of the reaction chamber 300 or a porous pad therein. That is, the detectable signal generator fixed to the reaction chamber 300 is lysed by penetration of the supernatant, at which point the lysed binder is combined with an analyte contained in the supernatant. The combined detectable signal generator-analyte becomes a movable product. If the supernatant flows into the reaction chamber 300, the detectable signal generator is excessively re-lysed at an early stage while re-lysis of the detectable signal generator is drastically reduced at a later stage. Conventional technologies have problems with deterioration in reproducibility of test results and concentration-response signal characteristics of analytes, depending on variation in re-lysis of the detectable signal generator and/or outflow rate of the detectable signal generator, since both a capillary force acting unit and another unit containing the detectable signal generator are co-present in a physical space. Such technologies also have restrictions wherein the detectable signal generator must be in a solid phase and fixed to the physical space. On the contrary, the exemplary embodiment separately uses a reaction chamber 300 containing the detectable signal generator and an analysis chamber 400 for capillary action, described below, thereby eliminating influences of re-lysis of a detectable signal generator and/or outflow rate of the detectable signal generator on capillary force. In addition, as a fluid sample (that is, a liquid specimen) is fed into the analysis chamber 400 after completing combination of the detectable signal generator with the analyte in a physically separated space, the detectable signal generator may be preferably present in either a liquid or a solid state.

A detectable signal generator refers to a material specifically reacting with an analyte provided in the reaction chamber 300 by any typical method. Examples of such detectable signal generator vary depending on the types of analytes. For instance, for antibody A as the analyte, the detectable signal generator may be a conjugate such as an antigen or antibody pre-linked with a labeling material such as a fluorescent material, wherein the antibody A and the detectable signal generator are first combined in the reaction chamber 300, a conjugate formed of the antibody A and the fluorescent material is fixed to the analysis chamber 400, using an antigen corresponding to the antibody A, followed by use of the conjugate for detection.

Labels of the detectable signal generator may include, for example, polymeric beads, metal colloids such as gold colloids or silver colloids, enzymes such as peroxidase, fluorescent materials, luminous materials, super paramagnetic materials, materials containing lanthanum (III) chelate, polymeric nano-particles, and radioactive isotope elements. However, the labels of the detectable signal generator are not particularly limited thereto.

The reaction chamber 300 may have a waste chamber 360 to store residues remaining after the reaction which were rinsed using a washer buffer in the washer chamber 330, impurities to be withdrawn, and the like. The impurities containing an un-combined detectable signal generator and/or analyte are moved to the waste chamber 360. Therefore, for example, for non-competitive analysis such as detection of specific antibodies, an un-combined detectable signal generator or analyte in the reaction chamber 300 is neither shifted to the analysis chamber 400 nor combined with a capture binder permanently fixed to a test region or a control region described below. Accordingly, a detectable signal generator-analyte complex is not bonded to the test region or the control region, thereby avoiding competitive inhibition of such bonding. Moreover, since an un-combined portion of the analyte is separated into the waste chamber 360, a "high-dose Hook effect" caused by a high concentration analyte is not observed. The waste chamber 360 is connected to the reaction chamber 300 through a channel 362. The channel 362 has a valve 361 which may be a normally closed valve described above.

The analysis chamber 400 is connected to the reaction chamber 300 through a valve 305 and receives a fluid from the reaction chamber 300 after the reaction is terminated.

The analysis chamber 400 is provided for antigen-antibody response or a specific biochemical reaction between biomaterials.

The analysis chamber 400 includes a holder 410 for receiving a fluid from the reaction chamber 300 after terminating a reaction; and a detection region 420 under capillary action, which consists of porous membranes, micro-pore structures or micro-pillars. The detection region 420 includes a test region 430 to which a capture binder is directly or indirectly fixed in order to assay analytes. The analysis chamber 400 may further have a control region 440 to which another capture binder, independent of the capture binder permanently fixed to the test region 430, is permanently fixed.

An end of the detection region 420 is extended to the holder 410 and, when a fluid fed from the reaction chamber 300 fills the holder 410, the extended end of the detection region 420 is submerged in the fluid. When fully charging the holder 410 with fluid, capillary force is applied in Direction A shown in FIG. 2, and a detectable signal generator-analyte complex moves along the detection region 420 in the same direction, that is, Direction A. The detectable signal generator-analyte complex is combined with a capture binder which is permanently fixed to the test region 430 and the control region 440 by antigen-antibody response or a specific biochemical reaction between biological materials. As a result, the detectable signal generator-analyte complex is entrapped in the test region 430 and the control region 440. After the fluid is completely shifted to the regions 430 and 440 by capillary force, the fluid is again delivered back into the holder 410 by centrifugal force applied in Direction B shown in FIG. 2, wherein the centrifugal force is generated by rotation of the micro-fluidic device. The direction of centrifugal force, Direction B, is opposite to the direction of capillary action, Direction A. Accordingly, compared to any conventional technique using capillary force applied in a single direction to react the fluid with a fixed reagent, a 2-fold increase in reaction time is achieved, in turn, remarkably enhancing reaction sensitivity.

A reaction cycle of the application of capillary force (Direction A) and centrifugal force (Direction B) is not limited to only one cycle but, after completely transporting the fluid back into the holder 410 by centrifugal force and stopping rotation of the micro-fluidic device, a portion of the detectable signal generator-analyte complex which was not combined with the capture binder is again combined with the other capture binder permanently fixed to the test region 430 and the control region 440 by capillary force in Direction A. After the fluid is completely shifted to the regions 430, 440 by a second application of capillary action, the fluid may be again delivered into the holder 410 using a second application of centrifugal force generated by rotation of the micro-fluidic device so that a portion of the analyte-first reagent complex which was not combined by the second capillary action may be repeatedly subjected to reaction. In one exemplary embodiment, a reaction cycle is repeated for the desired number of repetitions so as to sufficiently conduct the reaction, thus considerably improving detection sensitivity of analytes.

The analysis chamber 400 has a stoppage chamber 460 to receive a portion of the fluid which was not combined with the capture binder after the reaction in the test region 430 and control region 440. The stoppage chamber 460 is connected to the analysis chamber 400 via a channel 462. A valve 461 is mounted on the channel 462. The valve 461 may be a normally closed valve described above. After the reaction is sufficiently conducted, the valve 461 is opened and the fluid contained in the analysis chamber 400 is completely shifted to the stoppage chamber 460 using centrifugal force generated by rotation of the micro-fluidic device, thus terminating the reaction.

The capture binder refers to a capture probe to assay analytes and may include various materials such as antigen, antibody, enzyme, DNA, RNA, and the like depending on the subject analyte materials to be analyzed. For instance, if the analyte is a carbamate-based insecticide, the capture binder may be acetylcholine esterase (AChE), while if the analyte is an antigent, the capture binder may be a capture antibody for the antigen.

Figure 5:
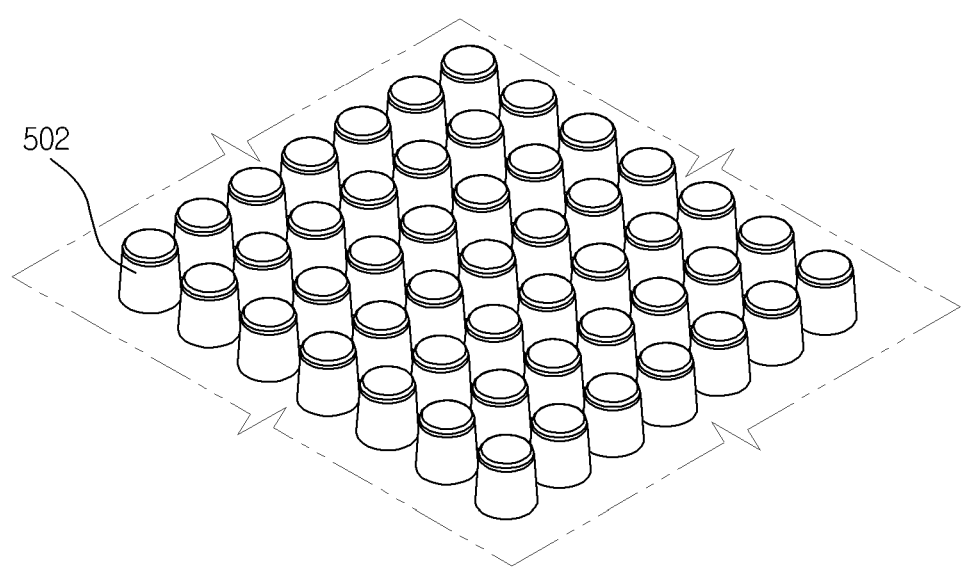
FIG. 5 is an enlarged view illustrating micro-pillars formed in a detection region according to an exemplary embodiment.

The detection region 420 to which the capillary force is applied must be optically transparent, and may have a cross-section in a circular or rectangular form. For the detection region 420 with a circular cross-section, an internal diameter of a capillary tube may range from approximately several micrometers to approximately 1 millimeter. A size of the capillary tube may be defined within a desired range sufficient to determine a red blood cell ratio, that is, hematocrit. The detection region 420 may be formed by any suitable materials as long as they have a small cavity volume and comprise very fine pores with a high bulk density. Examples of such materials may include porous membranes, micro-pore structures, micro-pillars, and the like. FIG. 5 shows micro-pillars 502 used for preparing the detection region 420.

Figure 6:
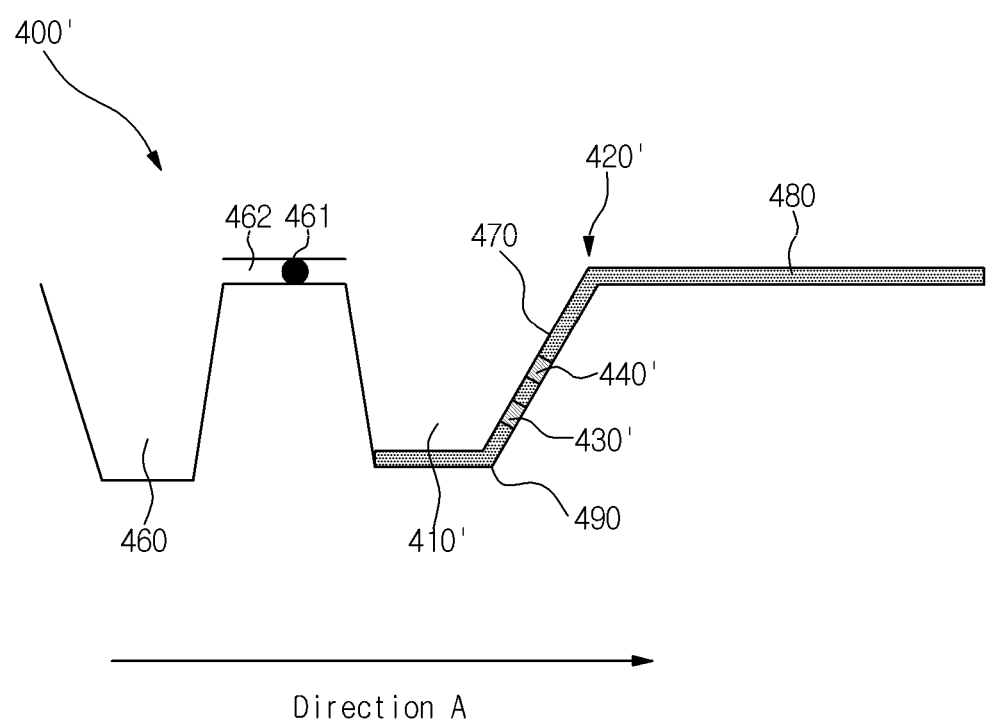
FIG. 6 is a side view illustrating an analysis chamber according to another exemplary embodiment.

FIG. 6 shows an analysis chamber 400' according to another exemplary embodiment. Referring to FIG. 6, a detection region 420' having a test region 430' and a control region 440' is partially inclined relative to the Direction A for capillary action. More particularly, an end of the detection region 420' coming into contact with a holder 410' forms an upward inclination unit 470 in which the test region 430' and the control region 440' are present, while the other unit 480 of the detection region 420' is straight. The reason behind such configuration is that the end 490 of the detection region 420' coming into contact with the holder 410' is located below the test region 430' and the control region 440' so as to prevent overflow of the fluid exceeding capillary force by virtue of gravity.

Another exemplary embodiment provides a centrifugal micro-fluidic device for detection of an analyte from a liquid specimen, including: at least one micro-fluidic structure having multiple chambers, at least one channel through which the multiple chambers are connected together, and at least one valve for opening and closing the at least one channel; and a detection unit, wherein the device also has a reaction chamber for receiving a detectable signal generator to be combined with an analyte in the liquid specimen and an analysis chamber that is located downstream of the reaction chamber and includes a detection region to which a capture binder to be combined with a detectable signal generator-analyte complex is fixed, and wherein a fluid transported between the reaction chamber and the analysis chamber is controlled by the at least one valve, and wherein the detection region includes porous membranes, micro-pore structures or micro-pillars.

This exemplary embodiment is substantially identical to the above-described exemplary embodiment, except that the micro-fluidic structure is mounted on the micro-fluidic device. Hereinafter, particular characteristics and/or technical configurations of the above micro-fluidic device different from those described in the previous exemplary embodiment will be explained, while a detailed description of the same conditions may be omitted for brevity.

After an analyte contained in a fluid sample (that is, the liquid specimen) has been completely combined with a detectable signal generator in a reaction chamber 300, a valve 305 located between the reaction chamber 300 and an analysis chamber 400 is opened. Then, the fluid sample containing a detectable signal generator-analyte complex is delivered into a holder 410 of the analysis chamber 400. After filling the holder 410 with the fluid sample, the fluid sample moves along a detection region 420 by capillary action, wherein an end of the holder 410 comes into contact with the detection region 420. While moving along the detection region 420 in Direction A shown in FIG. 2, the detectable signal generator-analyte complex is combined with a capture binder permanently fixed to a test region 430 and a control region 440, for example by antigen-antibody response or a specific biochemical reaction between biomaterials.

As described above, the detectable signal generator may be present in a liquid or solid phase in the reaction chamber 300. When the detectable signal generator is present in a solid phase, the detectable signal generator fixed to the reaction chamber 300 is lysed by penetration of a supernatant, and the lysed binder is then combined with an analyte contained in the supernatant. The combined detectable signal generator-analyte becomes a movable product.

As described above, the movable product is separated into a detectable signal generator-containing portion and a capillary force-acting portion by physical separation, wherein the detectable signal generator-containing portion is entered into the reaction chamber 300 while the capillary force-acting portion is received in the analysis chamber 400. As a result, influences of re-lysis of the detectable signal generator and/or outflow rate of the detectable signal generator on capillary force may be favorably excluded. Furthermore, since the fluid sample is fed into the analysis chamber 400 after completing combination of the detectable signal generator with the analyte in a physically separated space, the detectable signal generator may be preferably present in either a liquid or a solid state. Transportation of the fluid sample containing a detectable signal generator-analyte complex from the reaction chamber 300 to the analysis chamber 400 is duly controlled by opening and closing a valve 305.

Figure 7:
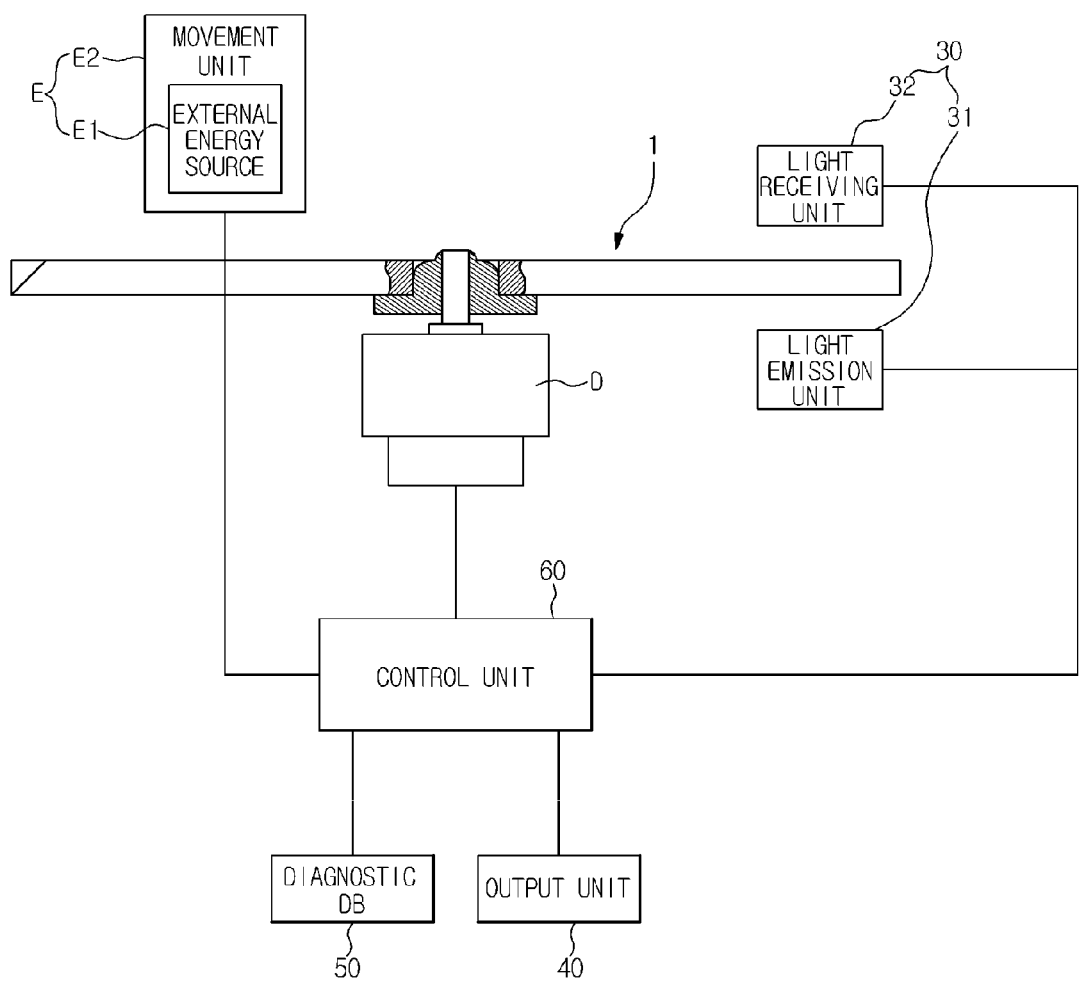
FIG. 7 is a block diagram illustrating a test system according to an exemplary embodiment.

FIG. 7 is a block diagram illustrating a test system, according to an exemplary embodiment.

Such a test system of the above exemplary embodiment includes a rotational driver D for rotating a disc-type micro-fluidic device 1, a valve switching unit E, a detection unit 30, an output unit 40, a diagnosis database (DB) 50, and a control unit 60 for controlling individual devices described above.

The rotational driver D rotates the disc-type micro-fluidic device 1 in order to apply centrifugal force thereto, enabling centrifugation of a sample and movement of a fluid, and also stops and rotates the same device 1 in order to move the analysis chamber 400 (see FIG. 2) to a desired position.

Although not shown in the drawing, the rotational driver D may further include a motor driving device for controlling an angular position of the disc type micro-fluidic device 1. For example, the motor driving device may have a stepper motor or a direct current (DC) motor.

The valve switching unit E is provided for opening and closing at least one valve (not shown) of the disc type micro-fluidic device 1, and includes an external energy source E1 and a movement unit E2 to move the external energy source E1 to any valve required to be opened.

The external energy source E1 may be selected from a laser source radiating a laser beam, a light emitting diode ("LED") radiating visible or infrared light, a xenon lamp, etc. In particular, the laser source may have at least one laser diode (LD).

The movement unit E2 may further include a driving motor (not shown) and a gear unit (not shown) equipped with the external energy source E1 to move the external energy source E1 above a valve required to be opened by rotation of the driving motor.

The detection unit 30 may be installed in plural to determine absorbance of the reaction chamber, and in one exemplary embodiment includes at least one light emission unit 31 and at least one light receiving unit 32 which is aligned with the light emission unit 31 to receive light penetrating the detection region 420 of the analysis chamber 400 (see FIG. 2) on the micro-fluidic device 1.

The light emission unit 31 may be a light source flashing at a specific frequency including, for example, a semiconductor light emitting device such as an LED or a laser diode (LD), a gas discharge lamp such as a halogen lamp or a xenon lamp, etc.

The light emission unit 31 is placed at a location above the micro-fluidic device 1 at which light emitted from the light emission unit 31 passes through the analysis chamber 400 and reaches the light receiving unit 32.

The light receiving unit 32 generates electrical signals according to an intensity of incident light and adopts, for example, a depletion layer photodiode, avalanche photodiode (APD), photomultiplier tube (PMT), etc.

In the present exemplary embodiment, the light emission unit 31 is located above the disc type micro-fluidic device 1, while the light receiving unit 32 is positioned below the disc type micro-fluidic device 1; however, the positions of these units may be switched. Also, a light path may be adjusted using a reflecting mirror or a light guide member (not shown).

The control unit 60 controls the rotational driver D, the valve switching unit E and/or the detection unit 30 to smoothly conduct operation of the test system, searches the diagnostic DB 50 and uses absorbance detected from the detection unit 30 and a standard curve stored in the diagnostic DB 50 so as to determine a concentration of an analyte in the supernatant contained in the analysis chamber 400 of the micro-fluidic device 1.

The output unit 40 outputs diagnosis results and information as to whether the diagnosis is completed or not, and may include a visible output device such a liquid crystal display (LCD), an audio output device such as a speaker, or an audio-visual output device.

Figure 8:
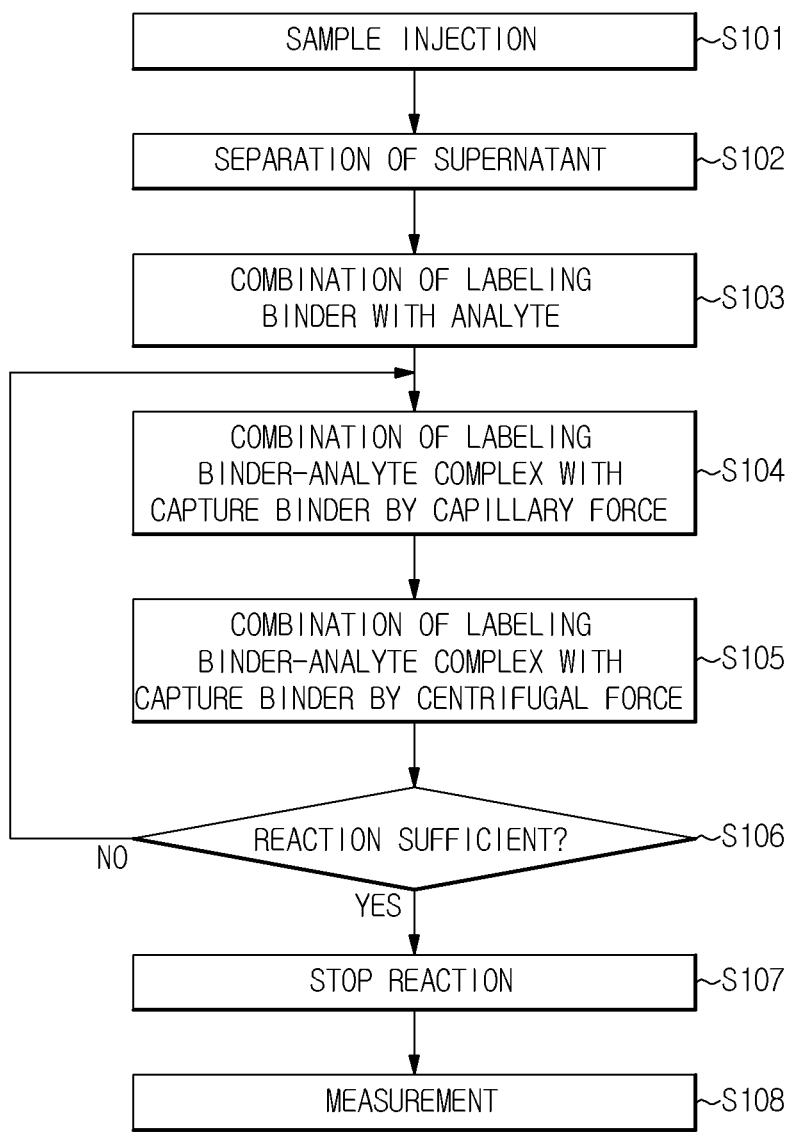
FIG. 8 is a flow chart explaining a method for detection of an analyte from a liquid specimen using a micro-fluidic device according to an exemplary embodiment.

The following description will be given of a method of detection of analytes in a liquid specimen, using the micro-fluidic device. FIG. 8 is a flow chart illustrating a method of detection of an analyte in a liquid specimen, using the micro-fluidic device, according to an exemplary embodiment. In this non-limiting exemplary embodiment, a process for blood analysis will be described in detail.

For example, whole blood sampled from a subject to be tested is introduced into a sample chamber 100 (S101), and the micro-fluidic device 1 is mounted on the rotational driver D.

Next, rotating the micro-fluidic device 1 at a low speed, the blood sample is delivered from the sample chamber 100 to the sample separation unit 200. The low speed may be, in one exemplary embodiment, a revolution speed generating centrifugal force suitable for moving a fluid. For example, the micro-fluidic device 1 may rotate with an accelerated velocity of approximately 1800 revolutions per minute for 11 seconds. By centrifugal force, the sample moves from the sample chamber 100 to the sample separation unit 200. The sample is transported from the sample chamber 100 to the sample separation unit 200 by centrifugal force.

Then, a centrifuging process is conducted (S102). The rotational driver D rotates the micro-fluidic device 1 at a high speed. Such high speed may be a revolution speed separating the blood into a serum or plasma as a supernatant and a precipitate (blood cells). For example, the micro-fluidic device 1 may rotate with an accelerated velocity of approximately 3600 rpms for about 160 seconds. As a result, relatively heavy blood cells are moved into the precipitate collector 220 while the supernatant remains in the supernatant collector 210.

Using the valve switching unit E, the closed valve 231 is opened. The rotational driver D rotates the micro-fluidic device 1 to generate centrifugal force. This centrifugal force causes the supernatant to move from the supernatant collector 210 to the supernatant metering chamber 250 via the channel 230. Since the valve 251 at an outlet of the supernatant metering chamber 250 is closed, the supernatant fills the supernatant metering chamber 250. Accordingly, if an amount of the supernatant is sufficient, the supernatant is contained in the supernatant metering chamber 250 in an amount corresponding to a volume of the supernatant metering chamber 250.

Next, the valve 251 is opened using the valve switching unit E, and the supernatant moves from the supernatant metering chamber 250 to the reaction chamber 300 by rotation of the micro-fluidic device 1. The rotational driver D may shake the micro-fluidic device 1 several times in right and left (clockwise and counter-clockwise) directions in order to combine the detectable signal generator with the analyte contained in the supernatant. As a result, a fluid sample (that is, a liquid specimen) containing a detectable signal generator-analyte complex is created in the reaction chamber 300 (S103).

Subsequently, by opening the valve 305 and rotating the micro-fluidic device, the fluid sample is moved into the holder 410 of the analysis chamber 400. After filling the holder 410 with the fluid sample, an end of the detection region 420 comes into contact with the fluid sample contained in the holder 410, in turn enabling capillary transfer of the fluid sample in the detection region 420 or 420', which consists of porous membranes, micro-pore structures or micro-pillars. The fluid sample containing the detectable signal generator-analyte complex moves along the detection region 420 or 420', and the detectable signal generator-analyte complex is combined with a capture binder permanently fixed to the test region 430 or 430' (S104). After the fluid sample completely passes through the detection region 420 or 420', the rotational driver D rotates the micro-fluidic device in order to pass the fluid sample back again through the detection region 420 or 420' by centrifugal force. Here, a portion of the detectable signal generator-analyte complex which was not combined with the capture binder by capillary force may be combined with the capture binder (S105). Therefore, compared to the conventional technique wherein an antigen-antibody response and/or a biochemical reaction is terminated only after fluid flow in a single direction, a reaction time in the present exemplary embodiment is remarkably extended, in turn, enhancing reaction sensitivity. In addition, as described above, the cycle of application of capillary force and centrifugal force used in the exemplary embodiment is not limited to one cycle, but may be repeated for the desired number of cycles, so as to sufficiently conduct the reaction. In other words, when rotation of the micro-fluidic device is stopped after complete delivery of the fluid sample into the holder 410 by centrifugal force, the fluid sample flows again along the detection region 420 by capillary action (S104). After complete movement of the fluid sample along the detection region 420, the fluid sample may be returned to the holder 410 using the centrifugal force generated by rotating the micro-fluidic device once more (S105).

When it is determined that the reaction is sufficiently conducted ("YES" in S106), the valve 461 connected with the holder 410 of the analysis chamber 400 is opened and the fluid sample is transported into the stoppage chamber 460 through channel 462 by rotation of the micro-fluidic device. After transportation of the fluid sample to the stoppage chamber 460, the reaction to combine the detectable signal generator-analyte complex with the capture binder is terminated and does not proceed any further (S107). Lastly, using the detection unit 30, absorbance of the detection region 420 in the analysis chamber 400 is determined. For analysis of end points, the absorbance is repeatedly measured at a defined distances to determine an absorbance during a saturated reaction. Based on a relationship between absorbance and concentration stored in the diagnostic DB 340, a concentration of each of substances to be analyzed is calculated.

Although a few exemplary embodiments have been shown and described in conjunction with accompanying drawings, it is clearly understood that the exemplary embodiments have been proposed for illustrative purpose only and do not particularly restrict the scope of the inventive concept. Accordingly, it will be appreciated by those skilled in the art that various substitutions, variations and/or modifications may be made in these exemplary embodiments, and such exemplary embodiments are not particularly restricted to particular configurations and/or arrangements described or illustrated above.

What is claimed is:

1. A centrifugal micro-fluidic device comprising:
at least one micro-fluidic structure comprising a chamber and at least one channel connected with the chamber; and
a detection unit,
wherein the chamber comprises a reaction chamber in which a detectable signal generator is combined with an analyte of a liquid specimen to create a detectable signal generator-analyte complex, and an analysis chamber located downstream from the reaction chamber,
wherein the analysis chamber comprises a detection region provided in the form of a strip where a capture binder is combined with the detectable signal generator-analyte complex, and a holder which is directly connected to the reaction chamber through a channel and carries a fluid provided from the reaction chamber, and the holder is disposed between the analysis chamber and a stoppage chamber which receives a portion of the fluid from the analysis chamber after a reaction is completed, wherein the detection region includes one of porous membranes, micro-pore structures and micro-pillars, and wherein the detection region is configured to utilize capillary force to move the fluid to a first end of the analysis chamber and the detection region is configured to utilize centrifugal force to move the fluid to a second end, which is opposite to the first end, of the analysis chamber.

2. The centrifugal micro-fluidic device according to claim 1, wherein the detection region contacts one end of the holder.

3. The centrifugal micro-fluidic device according to claim 1, wherein the detection region comprises a test region to which the capture binder is fixed, and a control region which is located downstream of the test region relative to a direction of capillary action and separated from the test region by a distance.

4. The centrifugal micro-fluidic device according to claim 3, wherein a section of the detection region including the test region and the control region is inclined in the direction of capillary action.

5. The centrifugal micro-fluidic device according to claim 1,
wherein the stoppage chamber is located downstream of the analysis chamber relative to a direction of centrifugal force.

6. The centrifugal micro-fluidic device according to claim 1, wherein the detectable signal generator is composed of an analyte specific binding member and a detectable signal generating member.

7. The centrifugal micro-fluidic device according to claim 1, wherein the detectable signal generator in the reaction chamber is contained in a liquid or dried solid state.

8. The centrifugal micro-fluidic device according to claim 1, wherein the detectable signal generator is selected from polymeric beads, metal colloids, enzymes, fluorescent materials, luminous materials, super paramagnetic materials, materials containing lanthanum (III) chelate, polymeric nano-particles and radioactive isotopes.

9. The centrifugal micro-fluidic device according to claim 1, wherein the detection unit detects and assays the detectable signal generator -analyte complex combined with the capture binder.

10. The centrifugal micro-fluidic device according to claim 1, wherein the detection unit comprises a light source unit and a light receiving unit that is aligned with the light source unit and receives light emitted from the light source unit that passes through the analysis chamber.

11. The centrifugal micro-fluidic device according to claim 1, further comprising a rotational body.

12. A centrifugal micro-fluidic device comprising:
a rotational body;
at least one micro-fluidic structure comprising a chamber, at least one channel connected with the chamber, and at least one valve for closing and/or opening the at least one channel; and
a detection unit,
wherein the chamber comprises a reaction chamber in which a detectable signal generator is combined with an analyte of a liquid specimen to create a detectable signal generator-analyte complex, and an analysis chamber located downstream from the reaction chamber,
wherein the analysis chamber comprises a detection region provided in the form of a strip where a capture binder is combined with the detectable signal generator-analyte complex, and a holder which is directly connected to the reaction chamber through a channel and carries a fluid provided from the reaction chamber, and the holder is disposed between the analysis chamber and a stoppage chamber which receives portion of the fluid from the analysis chamber after a reaction is completed, wherein the detection region comprises one of porous membranes, micro-pore structures and micro-pillars, and wherein the detection region is configured to utilize capillary force to move the fluid to a first end of the analysis chamber and the detection region is configured to utilize centrifugal force to move the fluid to a second end, which is opposite to the first end, of the analysis chamber.

13. The centrifugal micro-fluidic device according to claim 12, wherein the detection region contacts one end of the holder.

14. The centrifugal micro-fluidic device according to claim 12, wherein the detection region includes a test region to which the capture binder is fixed, and a control region which is located downstream of the test region relative to a direction of capillary action and separated from the test region by a distance.

15. The centrifugal micro-fluidic device according to claim 14, wherein a section of the detection region including the test region and the control region is inclined in the direction of capillary action.

16. The centrifugal micro-fluidic device according to claim 12, wherein the stoppage chamber is located downstream of the analysis chamber relative to a direction of centrifugal force.

17. The centrifugal micro-fluidic device according to claim 12, wherein the detectable signal generator is composed of an analyte specific binding member and a detectable signal generating member.

18. The centrifugal micro-fluidic device according to claim 12, wherein the detectable signal generator is contained in the reaction chamber in a liquid or dried solid state.

19. The centrifugal micro-fluidic device according to claim 12, wherein the detectable signal generator is selected from polymeric beads, metal colloids, enzymes, fluorescent materials, luminous materials, super paramagnetic materials, materials containing lanthanum (III) chelate, polymeric nano-particles and radioactive isotopes.

20. The centrifugal micro-fluidic device according to claim 12, wherein the detection unit detects and assays the detectable signal generator-analyte complex combined with the capture binder.

21. The centrifugal micro-fluidic device according to claim 12, wherein the detection unit comprises a light source unit and a light receiving unit that is aligned with the light source unit and receives light emitted from the light source unit that passes through the analysis chamber.

22. A centrifugal micro-fluidic device comprising:
at least one micro-fluidic structure comprising a chamber, at least one channel connected with the chamber, and at least one valve for closing and/or opening the at least one channel; and
a detection unit,
wherein the chamber comprises a reaction chamber in which a detectable signal generator is combined with an analyte of a liquid specimen to create a detectable signal generator-analyte complex, and an analysis chamber located downstream from the reaction chamber,
wherein the analysis chamber comprise a detection region provided in the form of a strip where a capture binder is combined with the detectable signal generator-analyte complex, and a holder which is directly connected to the reaction chamber through a channel and carries a fluid provided from reaction chamber, and the holder is disposed between the analysis chamber and a stoppage chamber which receives a portion of the fluid from the analysis chamber after a reaction is completed, wherein the at least one valve controls transportation of the fluid between the reaction chamber and the analysis chamber, wherein the detection region comprises one of porous membranes, micro-pore structures and micro-pillars, and wherein the detection region is configured to utilize capillary force to move the fluid to a first end of the analysis chamber and the detection region is configured to utilize centrifugal force to move the fluid to a second end, which is opposite to the first end, of the analysis chamber.

23. The centrifugal micro-fluidic device according to claim 22, wherein the detection region contacts one end of the holder.

24. The centrifugal micro-fluidic device according to claim 22, wherein the detection region comprises a test region to which the capture binder is fixed, and a control region which is located downstream of the test region relative to a direction of capillary action and separated from the test region by a distance.

25. The centrifugal micro-fluidic device according to claim 24, wherein a section of the detection region including the test region and the control region is inclined in the direction of capillary action.

26. The centrifugal micro-fluidic device according to claim 22, wherein the detectable signal generator is composed of an analyte specific binding member and a detectable signal generating member.

27. The centrifugal micro-fluidic device according to claim 22, wherein the detectable signal generator is contained in the reaction chamber in a liquid or dried solid state.

28. The centrifugal micro-fluidic device according to claim 22, wherein the detectable signal generator is selected from polymeric beads, metal colloids, enzymes, fluorescent materials, luminous materials, super paramagnetic materials, materials containing lanthanum (III) chelate, polymeric nano-particles and radioactive isotopes.

29. The centrifugal micro-fluidic device according to claim 22, wherein the detection unit detects and assays the detectable signal generator-analyte complex combined with the capture binder.

30. The centrifugal micro-fluidic device according to claim 22, wherein the detection unit includes a light source and a light receiving unit that is aligned with the light source unit and receives light emitted from the light source unit that passes through the analysis chamber.

31. The centrifugal micro-fluidic device according to claim 1, wherein the capillary force to move the fluid to the first end is directed towards a center point of the micro-fluidic device.

* * * * *